US006855678B2

(12) United States Patent
Whiteley

(10) Patent No.: US 6,855,678 B2
(45) Date of Patent: Feb. 15, 2005

(54) MEDICAL RESIDUE TREATMENT COMPOSITION COMPRISING A LITHIUM SALT

(76) Inventor: Reginald Reith Whiteley, 353 Pittwater Road, North Manly, New South Wales, 2100 (AU)

( * ) Notice: Subject to any disclaimer, the term of this patent is extended or adjusted under 35 U.S.C. 154(b) by 80 days.

(21) Appl. No.: 10/347,858

(22) Filed: Jan. 20, 2003

(65) Prior Publication Data

US 2003/0161758 A1 Aug. 28, 2003

Related U.S. Application Data

(63) Continuation of application No. PCT/AU01/00888, filed on Jul. 20, 2001.

(30) Foreign Application Priority Data

Jul. 21, 2000 (AU) .............................. PQ 8932

(51) Int. Cl.⁷ .............................. C11D 3/48; C11D 3/44
(52) U.S. Cl. ...................... 510/161; 510/382; 510/384; 510/391; 510/477; 510/480; 510/504
(58) Field of Search ................................ 510/161, 382, 510/384, 391, 477, 480, 504

(56) References Cited

U.S. PATENT DOCUMENTS

| 4,455,250 A | * | 6/1984 | Frazier .................... 510/106 |
| 4,808,569 A | * | 2/1989 | Chaudhuri et al. ............. 512/2 |
| 5,141,803 A | * | 8/1992 | Pregozen .................... 442/123 |
| 5,756,443 A | * | 5/1998 | Inoue et al. ................. 510/238 |
| 5,814,591 A | * | 9/1998 | Mills et al. .................. 510/238 |
| 5,925,681 A | * | 7/1999 | Crisanti et al. .............. 514/643 |
| 5,948,741 A | * | 9/1999 | Ochomogo et al. ......... 510/191 |
| 5,948,742 A | * | 9/1999 | Chang et al. ................ 510/191 |
| 5,962,001 A | * | 10/1999 | Rose et al. .................. 424/404 |
| 5,968,404 A | * | 10/1999 | Trinh et al. ................. 252/8.91 |
| 5,997,893 A | * | 12/1999 | Jampani et al. ............. 424/405 |
| 6,013,615 A | * | 1/2000 | Zhou et al. .................. 510/434 |
| 6,017,869 A | * | 1/2000 | Lu et al. ..................... 510/384 |
| 6,075,002 A | * | 6/2000 | Cheung et al. ............. 510/384 |
| 6,121,224 A | * | 9/2000 | Fonsny et al. .............. 510/384 |
| 6,200,941 B1 | * | 3/2001 | Strandburg et al. ......... 510/238 |
| 6,284,723 B1 | * | 9/2001 | Zhou et al. .................. 510/384 |
| 6,294,186 B1 | * | 9/2001 | Beerse et al. ............... 424/405 |
| 6,479,446 B1 | * | 11/2002 | Sherry et al. ............... 510/238 |

FOREIGN PATENT DOCUMENTS

| AU | A-76307/91 | | 4/1991 |
| AU | 76307/91 | * | 6/1992 |
| WO | WO 99/28428 | | 6/1999 |
| WO | WO 99/53010 | | 10/1999 |
| WO | 99/53010 | * | 10/1999 |
| WO | WO 99/60852 | | 12/1999 |
| WO | WO 02/07789 A1 | | 1/2002 |

* cited by examiner

*Primary Examiner*—Charles Boyer
(74) *Attorney, Agent, or Firm*—Levisohn, Berger & Langsam LLP

(57) ABSTRACT

The present invention relates to improved cleaning compositions and new methods for treating medical residue such as that remaining on surgical devices and appliances after use. The medical residue treatment compositions of the invention include: (a) at least one surfactant; (b) at least one solvent; (c) at least one co-solvent; (d) at least one nitrogen containing biocide; and (e) at least one organic chelating agent.

12 Claims, No Drawings

MEDICAL RESIDUE TREATMENT COMPOSITION COMPRISING A LITHIUM SALT

RELATED APPLICATIONS

This application is a continuation of PCT/AU01/00888, filed with the PCT on Jul. 20, 2001, which is based on Australian Patent Application, Serial Number PQ8932, filed Jul. 21, 2000, priority on both of which is claimed.

The present invention relates to improved cleaning compositions and new methods for treating medical residue such as that remaining on surgical devices and appliances after use.

BACKGROUND

The invention has been developed primarily to aid in the disinfection of sensitive fibre optical surgical instruments and will be described herein after with reference to this application. However, it will be understood that the invention is not limited to this particular field of use. For example, the compositions of the invention may be used to clean and sterilize other medical apparatus such as plastic tubing used for supplying medications and nutrients to patients during and following surgery.

One of the unexplained problems of modern surgery where fibre optic endoscope techniques are employed is the incidence of post operative (nosocomial) infections. These infections can usually be traced to a patient who previously had surgery using the same endoscope. This is despite the regular use by hospital staff of methods to clean and disinfect endoscopes thoroughly, using the best chemicals and cleaning techniques recommended by instrument manufacturers and medical microbiologists.

The current protocols for cleaning endoscopes begin with first washing the outside of a freshly used instrument with an enzyme containing neutral detergent. The detergent is then forced into the fine Teflon channels within the larger Teflon tubing of the instrument cover that enters a patient. Then the entire inner surface is carefully brushed in the presence of the detergent. The tubing is then rinsed with water and a disinfectant, either glutaraldehyde, peracetic acid, hydrogen peroxide or a mixture of the latter two. The disinfectant is then forced into the small Teflon channels and the entire instrument is soaked in the disinfectant solution where it remains for a recommended period. The instrument is then scrupulously rinsed with sterile water and dried under aseptic conditions.

There are number of disadvantages with the above recommended techniques. The first is that both glutaraldehyde and peractic acid have obvious well documented safety disadvantages. In addition peractic acid is expensive and destructive to components in the endoscopes. However, the main disadvantage is that recent research within the Medical Department of The University of Sydney has found that viable microbes may still remain on or in an apparatus which has been treated by these methods.

The major finding of the research referred to above was that in use endoscopes often become internally contaminated by bacterial "biofilms". These are distinctive, unique films deposited on inanimate surfaces by chemicals excreted by bacteria as part of their normal life processes, which serve as a natural protective home for bacteria of all classes. Previously biofilms have been identified and noted visibly or with the use of standard microscopes. However, by using Scanning Electron Microscopy (SEM) the inventor has now identified that the biofilm consists of a number of layers and most importantly there exists a thin layer of biofilm which is adjacent and attaches tightly to the surface of medical apparatus. This thin layer is herein referred to as the "basal layer" and can carry within it and/or associated with it active colonies of vegetative bacteria and blood born viruses such as the AIDS virus (HIV) and hepatitis B (HBV).

Importantly, bacteria and viruses found within biofilms are highly resistant to both chemical disinfectants and antibiotics. See "J W Costerton & P S Stewart, 'Battling Biofilms', Scientific American, July, 2001, pages 60–67". As reported in this paper Bateria located within biofilms can require from 25 to 1500 times the normal quantity of biocides and antibiotics to achieve complete sterilization. Thus, as will be appreciated this can greatly increase the cost of cleaning and wear and tear of the medical apparatus.

For general disinfection purposes it is possible to utilise very strong oxidising agents which can eliminate microbes as part of the disinfectant composition. However, if such agents are used to clean sensitive medical and dental equipment, problems can arise due to the highly corrosive properties of the compositions. Thus for medical and dental equipment and in particular fibre optic endoscopes it is necessary to use less corrosive disinfectant compositions. Although, as explained above, it has been found that adequate cleaning has not been achievable with these compositions. Whilst not wishing to be bound by theory this is thought to be because viable microbes embedded in the basal layer of the biofilm can survive precleaning and disinfecting with oxidising disinfectants, such as peracetic acid, and can become a potential source of post-operative infections.

Known compositions and methods that have been developed to clean and disinfect medical equipment include the use of neutral detergents such as Sonidet (Whiteley Industries Inc) and Endozyme (Davis & GECK Inc). These compositions and methods are generally effective in removing bulk soil and soft biofilm. However, Applicant has determined that these compositions do not remove, or completely kill the all of the viable microbes, in the basal layer of the biofilm.

The inventor has also previously developed a new glutaraldehyde concentrate for use with disinfecting and sterilising fibre optical surgical equipment. This new concentrate is described in international patent application number PCT/AU97/00734 and comprises:

(a) at least one mono or dialdehyde containing two to eleven carbon atoms;

(b) at least one glycol or polyol containing two to ten carbon atoms; and (c) at least one lithium based buffer soluble in said concentrate capable of maintaining the concentrate at pH 6 or above.

In this earlier invention the lithium buffer was used to control the pH of both the concentrate and its dilutions to within the desired biocidal effective range, ie at pH 6 or above. However, as noted above the usefulness of the composition of this earlier invention is restricted due to the presence of the glutaraldehyde.

Clearly there is an extensive body of knowledge on detergent processes and chemical disinfectants/sterilants, and application techniques, used in recent times to prevent, control and eliminate biofilms from an array of inanimate surfaces. This, however, is not applicable for totally removing and disinfecting/sterilizing biofilms found in endoscopes, and other more complex surgical instruments.

There is thus a clear need for a simple to use, non-corrosive, safe, near neutral chemical detergent compounds that will efficiently and reliably clean and disinfect endoscopes.

SUMMARY OF THE INVENTION

According to a first aspect of the invention there is provided a medical residue treatment composition which includes:

(a) at least one surfactant;

(b) at least one solvent;

(c) at least one co-solvent;

(d) at least one nitrogen containing biocide; and (e) at least one organic chelating agent.

Applicant has surprisingly found that the above compositions provide a simple to use, non-corrosive, safe, near neutral chemical detergent product that efficiently and reliably cleans and disinfects endoscopes and other-medical apparatus.

Whilst not wishing to be bound by theory, Applicant believes that;

a) the solvent and co-solvent act to swell the biofilm, b) the organic chelating agent in combination with the surfactant increases the ability of the nitrogen containing biocide to penetrate the biofilm, and c) the organic chelating agent in combination with the nitrogen containing biocide act to work synergistically to dislodge the biofilm and/or kill the microorganisms therein.

The use of chelating agents in biocidal formulations is known. For example they have been used to soften water and to react with divalent metal linkages on biological surfaces. However, it has now been surprisingly found that the presence of chelating agents substantially increases the ability of certain biocidal formulations to dislodge biofilms and or to kill microorganisms therein.

Organic Chelating Agents

The medical residue treatment compositions of the present invention may include one or more organic chelating agents. In a preferred embodiment the compositions of the invention may include two or more organic chelating agents. In a particularly preferred embodiment the compositions of the invention may include two or three organic chelating agents.

Any suitable organic chelating agents which either enhances the biocidal effect of the composition and/or enhances the ability of the composition to remove or penetrate biofilm may be included in the composition of the invention.

In addition to enhancing biocidal action of the overall composition and the penetration or removal of the biofilm, the organic chelating agents may also act as buffers to regulate the pH of the compositions.

In a preferred embodiment, the composition of the invention, includes at least one organic chelating agent which is a lithium containing compound. In fact the research conducted in association with the development of this invention indicates that the use of lithium containing compounds produces biocidal formulations which are superior as compared to those including either sodium or potassium compounds. This is believed to be due to the ability of the lithium ion to react with organic cell material in a similar manner as a hydrogen ion. Whilst not wishing to be bound by theory it is thought that the lithium ion, by its innate ability to form both ionic and covalent bonds with organic materials, can interpose in biological reactions taking place during cell reproduction and can thus interfere or inhibit one or more essential steps in protein synthesis.

Suitable lithium containing compounds that may be used in the composition of the invention include known lithium based buffers. The lithium containing compounds may be included in the composition of the invention in the form of lithium salts. Examples of lithium containing compounds include the lithium salts of hydroxyorganic or organic acids, the lithium salts of a carbonate or bicarbonate or mixtures thereof, lithium lauryl sulphate, lithium hydroxide, lithium triphosphate, lithium lactate, lithium citrate, lithium tartrate, lithium methylmethacrylate, lithium glycolate, lithium acetate and lithium phosphate. Lithium salts of a carbonate or bicarbonate used singly or in admixture are especially preferred.

In a particularly preferred embodiment, the composition of the invention, includes at least one chelating agent selected from the lithium salts of carboxylated and substituted diethylamine, or substituted derivatives of ethylenediamine of nitrilotriacetic acid, lithium lactate, dilithium citrate and trilithium trinitriloacetate.

The amount of organic chelating agent to be included in the composition of the invention needs to be sufficient to either enhance the biocidal effect of the composition and/or enhance the ability of the composition to penetrate or remove the biofilm. However, when the organic chelating agents are also added for an additional purpose, such as to act as a buffer, then additional amounts of these agents may be required for these purposes.

In a preferred embodiment, the composition of the invention, includes at least one organic chelating agent present in an amount from 0.05% to 20% by weight, preferably 0.5% to 5.0% by weight.

In the embodiments where the chelating agent is a lithium compound the amount of the compound added to the composition of the invention is sufficient to give a lithium ion concentration of between 50 and 15,000 parts per million. In a more preferred embodiment the concentration of lithium containing compound is sufficient to give a lithium ion concentration of between 250 and 2500 parts per million.

Examples of preferred lithium containing compounds and their preferred concentration ranges include: lithium bicarbonate, 0.05%–10.0% by weight; lithium carbonate, 0.05%–25.0% by weight; lithium phosphate, 0.10%–10.0% by weight; lithium glycolate, 0.05%–5.0% by weight: lithium lactate, 0.05%–5.0% by weight; lithium citrate, 0.05%–7.5% by weight; lithium tartrate, 0.05%–5.0% by weight; lithium methylmethacrylate, 0.05%–5.0% by weight; lithium benzoate, 0.05%–2.5% by weight; lithium lauryl sulphate, 0.05%–4.0% by weight; lithium alkylarylsulphonate, 0.05%–10.0% by weight; Lithium Dowanol 3B0 dialkyl (C2–8) diphenoloxide disulfonate, 0.05%–10.0% by weight.

Nitrogen Containing Biocides

The medical residue treatment compositions of the present invention may include one or more nitrogen containing biocides. In a preferred embodiment the compositions may include two or more nitrogen containing biocides. In a further embodiment the composition may include three or more nitrogen containing biocides.

Any nitrogen containing biocide that exhibits biocidal effect against microorganisms may be included in the composition of the present invention. The nitrogen containing biocide may or may not also act as a surfactant with regard to the removal of the biofilm. In a preferred embodiment, a nitrogen containing biocide may act as both a biocide and as a surfactant. Suitable nitrogen containing biocides include biocides containing primary, secondary or quaternary nitrogen groups. In a preferred embodiment, the composition of the invention, includes at least one nitrogen containing biocide which is an amine derived biocide.

Examples of suitable nitrogen containing biocides include alkyl (C8–14) dimethyl benzylammonium halides, dialky (C4–10) di and trimethylbenzyl or ethylbenzyl ammoniun halides, alkyl (C10–18) amine halides or other recognized commercial quaternary ammonium halides, including chlorhexidine salts and benzethonium chloride (Hyamine 1622).

Further examples of suitable nitrogen containing biocides include alkyl (C8–18) dimethylbenzyl ammonium chloride, cetyl trimethyl ammonium bromide, cetyl pyrimidium bromide, cetyl pyrimidium iodide, dimethyl dialkyl (C6–18) ammonium chlorides, chlorhexidine, diacetate, chlorhexidine digluconate, dodecylamine hydrochloride, dodecylamine gluconate, dimethyldodecylamine hydrochloride or glycolate, methyl bisthiocyanate, betabromo betanitrostyrene, tetrachloro isonaphalonitrile, 2-bromo-2-nitro-1,3-propanol, 5-chloro-4-isothiazolin-3one and 2-methyl-4-isothiazolin-3one.

The compositions of the invention may include any concentration of nitrogen containing biocides which exhibit biocidal effect against the classes of microorganisms normally found in the applications envisaged for the invention. The amount or concentration of nitrogen containing biocides to include in the composition may be determined in accordance with the Minimum Inhibitory Concentration (MIC) of the individual components towards selected classes of microorganisms. Where more than one nitrogen containing biocide is used in the composition, the concentration of biocides to be include in the composition may be determined by testing biocidal activity using other methods appropriate for the intended use of the composition.

In a preferred embodiment, the composition of the invention, includes at least one nitrogen containing biocide present in an amount from 0.025% to 20% by weight of the final composition. In a more preferred embodiment, the composition of the invention, includes at least one nitrogen containing biocide present in an amount from 0.10% to 20% by weight of the final composition, more preferably from 0.5% to 20% by weight, yet more preferably from 2.5% to 7.5% by weight.

Surfactants

The medical residue treatment compositions of the present invention may include one or more surfactants. In a preferred embodiment the compositions include one or more low energy surfactants. In a further embodiment the compositions may include three or more surfactants. The surfactants may be added singly or in admixture when preparing the compositions of the invention.

Any surfactant that enhances the ability of the composition to penetrate or remove biofilm may be included in the composition of the present invention. The surfactant should be compatible with the nitrogen containing biocides. Suitable surfactants include known anionic, cationic amphoteric, zwitterionic, non-ionic surfactants, alkyl glucosides, fatty amine ethoxylates, alpha fatty acid methyl esters, difatty acid amide quaternary molecules, monoalkyl phosphate ethers and cicyl succinic anhydrides.

Preferably, the surfactants are very low surface tension surfactants. It is especially preferred that the surfactants exhibit an air water surface tension of less than 28 dyne/centimeter.

The composition of the invention may include any of the known non-ionic surfactants. In a preferred embodiment, the composition of the invention, includes at least one non-ionic surfactant which is a low foaming non-ionic surfactant. Examples of such surfactants include poly (3–16) ethoxylates of alkyl (C8–18) alkanols, poly (3–16) ethoxylates of alkyl (C6–14) phenols and sulfate and phosphate esters thereof, commercial surfactants derived from block polymers of ethylene and/or propylene oxides with or without small alkyl chain substitutions on the polymer chain or mixtures thereof, and alkyl (C8–18) amine oxides.

In instances where high foam is acceptable, non-ionic surfactants such as alkyl (C8–18) amine oxides may be suitable. Preferably, when high foam non-ionic surfactants are used, a defoaming agents such as decanol and dodecanol may be also included in the composition of the invention.

In a preferred embodiment, the composition of the invention, includes at least one anionic surfactant selected from an anionic surfactant including an aryl (C8–18) sulphates or sulphonates, alkyl aryl (C4–18) single or dual chain benzyl or naphthyl sulphonates or substituted biphenyl and biphenyloxide mono and disulphonates. Examples of such surfactants include but are not limited to mono sulphonated alkyl diphenyl, di sulphonated alkyl diphenyl, mono sulphonated diphenyloxide, di sulphonated diphenyloxide, alkyl naphthalene sulphonate, dialkyl naphthalene sulphonate, acidic esters of alkyl phenol and allyl phenol polyethoxylates.

The composition of the invention may include an anionic surfactant in the form of the salt of a cation provided that it is compatible with the other components of the composition. Preferably, the anionic surfactant is included in the form of a sodium, potassium, ammonium, alkanolamide or lithium salt. In a preferred embodiment the anionic surfactant is a lithium salt of an anionic surfactant.

In instances where high foam is acceptable, the anionic surfactant may be lithium or sodium dodecyl sulphate or an alkyl (C8–18) sulphonate.

In some embodiments of the invention a surfactant other than an anionic or nonionic surfactant may be included in the composition. For example the surfactant may be selected from any one or more of a C10–C18 amphoteric surfactant or an ethylene oxide condensate of an amine derived surfactant.

In a particularly preferred embodiment, the composition of the invention, includes at least one surfactant that has at least one nitrogen group either as a primary, secondary or quaternary nitrogen group. Such surfactants may also act as biocidal surfactants. The action of these biocidal surfactants may be aided by the presence of additional surfactants.

In a particularly preferred embodiment, the composition of the invention, includes at least one surfactant selected from an alkyl polysaccharide, a nonionic surfactant containing from 8 to 18 carbon atoms and/or from 6 to 12 moles of ethyleneoxide, an amine oxide containing from 12 to 18 carbon atoms, an ethoxyalte alkyl amine containing from 10 to 14 carbon atoms and 1 to 6 mole of ethylene oxide, an alkyl (C8–12) dimethyl benzyl amine halide, and lauric mono, di or triethanolamine.

In a preferred embodiment, the composition of the invention, includes at least one surfactant present in an amount from 0.01% to 20.0% by weight, more preferably from 0.1% to 15.0% by weight, yet more preferably from 0.5% to 15% by weight.

Solvents

Any suitable solvents may be used in the medical residue treatment compositions of the invention. In a preferred embodiment, the composition of the invention, includes at least one solvent selected from one or more low molecular weight polar water soluble solvents chosen from primary or secondary alcohols, glycols, esters, ketones, aromatic alcohols and cyclic nitrogen solvents containing 8 or less carbon atoms. In a particularly preferred embodiment, the composition of the invention, includes at least one solvent selected from a glycol or alkanol or a derivative thereof. Any glycol or alkanol which is compatible with the other components of the composition may be included. Preferably water soluble low molecular weight alkanols, glycols and their esters having between 2 and 20 carbon atoms. More preferably the glycol is a polypropylene or polyethylene glycols having between 2 to 9 carbon atoms. Preferred glycols may be selected from the lower molecular weight polyethylene glycols. Examples of suitable glycols include triethyleneglycol and dipropylene glycol.

In a preferred embodiment, the composition of the invention, includes at least one solvent selected from but not limited to C1–6 alcohols, esters, ethers, ketone, glycols and their methyl and ethyl esters and ethers, aromatic alcohols containing 8 or less carbon atoms, pyrrolidone and methyl pyrrolidone.

In a preferred embodiment, the composition of the invention, includes at least one solvent present in an amount from 0.5% to 25% by weight and more preferably from 1.0% to 20% by weight.

Co-Solvents

Any suitable co-solvents may also be used in the medical residue treatment compositions of the invention. In a preferred embodiment, the composition of the invention, includes at least one co-solvent selected from any suitable low molecular weight amine, amide or amide or their methy or ethyl derivative. In a particularly preferred embodiment, the composition of the invention, includes at least one co-solvent selected from one or more amines or amine derivatives chosen from but not limited to acetamide, acetyl acetamide or diethylacetamine, pyrrolidone and methyl pyrrolidine, urea, and/or mono, di and triethanolamine and isopropanolamine or their halides.

In a preferred embodiment, the composition of the invention, includes at least one co-solvent present in an amount from 0.5% to 25% by weight and more preferably from 1.0% to 20% by weight.

Carrying Solvents

The medical residue treatment compositions of the present invention may also include at least one carrying solvent. Any carrying solvent which is compatible with the other components of the composition may be included. For example the carrying solvent may be a small polar solvent.

In a preferred embodiment, the composition of the invention, includes at least one carrying solvent selected from any one or more of water, methanol, ethanol, propanol and isopropanol, C1–C8 esters of organic acids and hydroxy organic acids, C2–C8 ketones, mono, di and triglycol ethers containing from 4 to 14 carbon atoms and their molecular variants, aromatic alcohols such as phenol, benzyl alcohol, ethylphenol, phenoxyethanol and nitrogen containing solvents such as pyridine, pyrollidone and their C1–C12 derivatives, and urea. Examples other suitable carrying solvents include any of those used in the manufacture of industrial detergents, solvent cleansers, paint strippers and both ink and varnish remover but which are not highly corrosive or toxic or damaging to medical apparatus such as tubing and organic components of endoscopes.

Enzymes

In another preferred embodiment the medical residue treatment compositions of the present invention may also include at least one enzyme. The enzymes may aid the removal of the biofilm by destroying proteinaceous glycoproteins and polysaccharides. Any enzyme which is compatible with the other components of the compositions may be included. Examples of suitable enzymes include hydrolytic enzymes amylase, pectinase, protease, papaine and combinations thereof.

The medical residue treatment compositions of the invention accomplish a major advance in two respects. Firstly it provides a medical residue treatment composition and method for effective removal of biofilms formed by major infective organisms found in typical surgical hospital situations. Secondly it provides a composition and method for achieving sterile surfaces without the use of a toxic, costly chemical biocide based on either glutaraldehyde or peracetic acid.

The medical residue treatment compositions of the invention also offer the opportunity for simplified methods requiring less supervision to guarantee consistent sterile results from reprocessing of endoscopes and other surgical instruments. There will also be reduced opportunity for bacteria, and presumably virus, to become resistant to biocides.

Moreover simplification and increased reliability of medical residue treatment compositions provides significant opportunity to fully mechanize reprocesssing operations with less complicated and less expensive processing machinery. For example, it can avoid the need to use machinery that requires an in-built fume extraction for neutralization or adsorption of unwanted vapors, which is the case when glutaraldhyde, peracetic acid or hydrogen peroxide are used.

The following examples illustrate some preferred embodiments of the invention. However, it should be understood that the following examples are illustrative only and should not be taken in any way as a restriction on the generality of the invention as described above.

EXAMPLE 1

The following example is a comparative example to illustrate the effectiveness of the medical residue treatment composition of the invention when compared to other medical residue treatment compositions.

To establish a workable but representative model of the problem of residual biofilms, the common pathogen *Escherichia coli*, found in the bowel of a hospital patient with virulent diarrhoea, was used as a test organism. A culture of *Escherichia coli* was circulated through Teflon tubing of the type used in one common brand of endoscopes at a controlled rate by a pump. Circulation was continued at constant temperature until a definite biofilm had formed within the tubing. Medical residue treatment compositions were then circulated for a ten (10) minute period at room temperature (20°–23° C.). This was followed by a sterile water rinse. The tubing was then filled with sterile phosphate buffer solution which was then transferred to sterile culture medium and incubated. Viable organisms were then counted. Tests were run in banks of 5 using the same culture, tubing and precise pumping rate.

The number of surviving organisms proved a reliable and quite representative means of determining the effectiveness of detergents to penetrate and disinfect residual biofilms.

In the first series of tests, a series of common detergents used in hospitals were employed with the following results:

TABLE 1

Common Detergents

| Detergent Type | Initial Culture cfu/ml | Recovered Bacteria cfu/ml |
|---|---|---|
| Control - no detergent | 4 log | 4 log |
| Neutral Nonionic | 4 log | 2.5 log |
| Enzymatic | 4 log | 3.4 log |
| Alkaline food cleaner | 4 log | 3.5 log |
| Mild acid bath detergent | 4 log | 3.4 log |

A second series of tests were then conducted using prior art disinfectant solutions and compositions of the invention. Applicant repeated the method as outlined for the common detergents above. The results of these tests are tabulated below:

TABLE 2

Disinfectant Studies

| Disinfectant Type | Initial Culture cfu/ml | Recovered Bacteria cfu/ml |
|---|---|---|
| Neutral quaternary | 4 log | 0.5 log |
| Neutral surface disinfectant[1] | 4 log | 0.2 log |
| Oxidising detergent | 4 log | 0.1 log |
| Acidic detergent[2] | 4 log | 0 log |
| Surfactant/lithium composition[3] | 4 log | 0 log |

[1] This is a neutral detergent based upon a glycol-quaternary-nonionic-EDTA combination which is strongly virudidal as well as bactericidal.
[2] A combination of a glycol, a lithium buffered hydroxy acid, a chelating agent and a non-ionic surfactant with a pH of 2–3 undiluted or 3–5 diluted.
[3] The following model composition employed at a dilution of 1 in 10 (10%) at room temperature:

| Ingredient | Amount % by weight |
|---|---|
| Dobanol 916 (alkyl (c8–10) poly (6) ethoxylate | 1.0 |
| Triethylene glycol | 2.5 |
| Trilithium EDTA | 1.0 |
| Benzalkonium chloride | 0.5 |
| Water | 95 |

The acidic detergent[2] and surfactant/lithium composition[3] are compositions according to the invention and were effective in killing the microorganisms in the biofilm. However, the basal layer of the biofilm remained largely intact.

EXAMPLE 2

This example is a further comparative example which also illustrates the effectiveness of the medical residue treatment composition of the invention. The testing protocol in this example duplicates the conditions of use and maintenance of endoscopes of all types.

Separate bacterial cultures of *Erischeria coli* and *Pueudomonas aeruginosa* were prepared and held at a defined culture density range of cfu/mL (colony forming units per milliliter) over the period of each test.

Lengths of both new Teflon endoscope tubing were provided by endoscopic equipment suppliers. Used endoscope tubing was provided by the service departments of the endoscope suppliers and by the Endoscopy Department of a public hospital when tubing was deemed to have reached the end of its useful life.

Lengths of tubing were connected to the culture and were maintained at constant temperature and the culture was circulated through the tubing by a peristaltic pump at constant adjusted flow rate. The tubing was exposed to the constant flow of bacterial culture for either 24 hours or 6 days. The tubing was then removed, rinsed in sterile PBS (which was kept for later examination for the number of cells recovered in the rinse) then cut asceptically into smaller pieces of uniform size. Following this the tubing was tested in various ways to evaluate the quantity, properties and removability of the resultant biofilm within the tubing.

Initially surface deposits were viewed by either bifocal microscope after being suitably stained and the stain fixed. Alternatively, or in addition the tubing was further dissected into smaller pieces to be appropriately resin set for SEM examination and photography.

In the first series of experiments three currently marketed enzyme containing detergents were used to clean freshly generated biofilms as recommended and the number of bacterial still resident in tubing after water rinsing was determined. The results of these tests are shown in Table 3.

TABLE 3

Efficacy of Enzyme Based Detergents

| Detergent Type | Initial Culture cfu/ml | Recovered Bacteria cfu/ml |
|---|---|---|
| Control, no detergent | 7.7 | Not Applicable |
| Nonionic Detergent | 7.7 | Log 4.5 |
| Enzyme Detergent A | 7.7 | Log 4.0 |
| Enzyme Detergent B | 7.7 | Log 2.6 |
| Enzyme Detergent C | 7.7 | Log 3.4 |

As noted from the results in Table 3 there was no practical difference between a normal neutral detergent and various enzyme based detergents as far as removing bacteria from tubing.

A second series of tests were then conducted using a range of common types of industrial detergents to assess alternatives for removing fresh biofilm. The results of these tests are shown In Table 4.

TABLE 4

Efficacy of Industrial Detergents

| Detergent Type | Initial Culture cfu/ml | Recovered Bacteria cfu/ml |
|---|---|---|
| Control - no detergent | 7.8 | Not Applicable |
| Nonionic pH 8.5 | 7.8 | 2.9 |
| Alkaline food cleaner pH 12 | 7.8 | 3.5 |
| Mildly acidic pH 4.5 | 7.8 | 3.1 |
| Strongly acidic pH 2.1 | 7.8 | 1.8 |

Again, as shown by the results in Table 4, significant numbers of bacteria survived routine cleaning where biofilms exist.

This latter procedure was repeated with an additional 13 types of detergents which are currently used for various medical, dental and industrial cleaning operations. Each detergent was used at the concentration as recommended by the manufacturers under ambient (20–22 C) conditions for 10 minutes which is the normal time used for cleaning endoscopes. The results of these tests were similar to those shown in Table 4.

The choice of detergent was limited, as the majority of commercially available products are likely to damage the components of the endoscopes or to prove toxic to humans. However, the detergents tested included very mildly alkaline, mildly alkaline, neutral, mildly acidic, strongly acidic, soluble solvent containing detergents and enzyme containing neutral detergents and combinations thereof.

SEM photographs prepared after cleaning dramatically showed what was suspected. None of the detergents tested removed the basal layer. The amount of the soft EPS comprising the bulk of the biofilm removed varied depending on the detergent or combination of detergents used. The detergents which include an oxidizing agent releasing peracetic acid and a patented solvent containing cleaner/disinfectant gave the best results but did not dislodge the basal layer.

Interestingly, the detergent which included the oxidizing agent releasing the peracetic acid in aqueous solution left some EPS clearly hardened and showing some of the structure of the original biofilm but no damage to the underlying basal layer. The patented near neutral detergent left only intact basal film. All three enzyme containing detergents left a varying amounts of EPS without damaging the basal layer of biofilms.

From the results of these tests it is clear that removing biofilms from Teflon and IV PVC medical tubing is a different and more difficult challenge than those for which known detergents have been designed.

A third series of tests were conducted to determine the affect of the major classes of biocidal-cleansers on biofilms using Medical PVC tubing as the test model with the results in Table 5.

TABLE 5

Disinfectant Studies

| Different Type Bacteria | Initial Culture cfu/ml | Recovered Bacteria cfu/ml |
| --- | --- | --- |
| Neutral Quaternary | Log 9 | Log 0.8 |
| Amine Surface Disinfectant | Log 9 | 0.7 |
| Oxidizing Detergent, PAA | Log 9 | 0.2 |
| Acidic Detergent* | Log 9 | 0.5 |
| Viraclean** | Log 9 | 0.1 |

*Combination of glycol, glycollic acid, amine, EDTA acid, sold as food cleanser disinfectant in aqueous solution.
**Patented aqueous solution containing lithium EDTA, glycol, amine biocide, nonionic surfactant While no disinfectant completely killed all organisms there was an improvement over cleaning compounds previously tested. Viraclean gave the better performance. However, not even this product killed all of the microrganisms.

EXAMPLE 3

The following medical treatment compositions in accordance with the present invention were prepared:

Composition 1

| Ingredient | Amount % by Weight |
| --- | --- |
| Pure water | 72.0 |
| Dodecylamine hydra-iodide | 7.5 |
| Lauryl poly (10) poly ethoxylate | 5.0 |
| n-methyl pyrrolidone | 7.0 |
| Ethyldiglycol | 7.0 |
| Lithium ethylenediaminetetraacetate | 1.5 |
| PH 8.0–8.5 | |

Composition 2

| Ingredient | Amount % by weight |
| --- | --- |
| Pure water | 68.0 |
| Cetyltrimethylamine hydrobromide | 10.0 |
| Lauric (C12–14) ethanolamide | 5.5 |
| Acetylacetamide | 8.5 |
| Propyleneacetate | 5.0 |
| Lithium citrate | 1.5 |
| Trilithium nitrilotriacetate | 1.5 |
| PH 8.5–9.0 | |

Composition 3

| Ingredient | Amount % by weight |
| --- | --- |
| Pure water | 68.5 |
| Chlorhexidine diacetate | 4.5 |
| Dipropyleneglycol | 12.5 |
| Lauryldimethylamineoxide | 3.0 |
| Alky (C8–10) poly (6–8) ethoxylate | 2.0 |
| Monoethanolamineacetate | 6.0 |
| Lithium lactate | 3.5 |
| PH 8.5–9.0 | |

Composition 4

| Ingredient | Amount % by weight |
| --- | --- |
| Pure water | 65.5 |
| Alkyl (C8–10) benzyldimethylamine hydrochloride | 10.0 |
| Alkylpolysaccharide | 6.5 |
| Benzylalcohol | 4.0 |
| Dimethylacetylacetamide | 5.0 |
| Dipropyleneglycolmethylether | 6.0 |
| Lithium citrate | 1.5 |
| Lithium2 diethyaminetetraacetate | 1.5 |
| PH 8.0–8.5 | |

Each of these compositions were made by mixing the ingredients in the order listed and adjusting the pH to the level noted by use of the alkali or acid component of the chelating agent.

Each compostion is intended to be diluted with either water, ethanol or isopropanol to 1 to 10 percent by volume according to need with the particular method of use, normally 2.5 to 5.0 percent by volume for endoscope cleaning.

To test the effectiveness of these compositions the procedure outlined in Example 2 were repeated. The results of these tests showed a total kill of residual organisms on tubing treated by each composition. In other words after treating tubing with each of these compositions the internal surface of the tubing was sterile as well as free from biofilm. Accordingly, these formulations each achieve quantitative removal of biofilm from Teflon and medical PVC tubing when used as directed.

To test the effectiveness of the above compositions the internal surfaces of the two types of tubing cleaned by the compositions were scraped and swabbed to locate any possible bacteria. However, the internal surfaces were found to be free of recoverable, hence infective bacteria. This result was obtained after a 10 minute soaking or circulating time of the tubing in a test composition at ambient temperature, the requirement in modern surgical practice. Further the formulations developed were essentially free from operating hazard and much safer to use than the current range of chemicals produced and approved internationally for routine use on endoscopes.

EXAMPLE 4

Applicant also prepared the following medical residue treatment compositions in accordance with the present invention:

General Surgical Detergent

| Ingredient | Amount % by weight |
| --- | --- |
| Dobanol 916 (Shell Chemicals Inc.) (Alkyl C8–10) poly (6) ethoxylate) | 0.25 |
| Triethylene glycol | 1.0 |
| Lithium lactate | 0.9 |
| Lithium lauryl sulphate | 0.15 |
| Octylphenol poly (10) ethoxylate | 0.15 |
| Trilithium ethylenediamine tetra acetate | 0.05 |
| Urea hydrobromide | 0.35 |
| Cetyl trimethyl ammonium bromide | 0.3 |
| Dialkyl (C8–10) dimethylbenzylammonium chloride | 0.3 |
| Water (deionised) | Balance |

Endoscope Detergent

| Ingredient | Amount % by weight |
| --- | --- |
| Alkyl (C8–11) poly (5–8) ethoxylate | 0.15 |
| Alkyl (C11–14) poly (10–16) ethoxylate | 0.15 |
| Ethylene glycol diethylether | 7.0 |
| n-methyl pyrrolidone | 5.9 |
| Lithium citrate | 1.5 |
| Trilithium EDTAt | 0.25 |
| Alkyl (C9–10) dimethylbenzylammonium chloride | 3.5 |
| Isopropanol | 7.5 |
| Lithium methylmethacrylate | 0.25 |
| Water | Balance |

Powdered Oxidising Detergent-Disinfectant

| Ingredient | Amount % by weight |
| --- | --- |
| Sodium perborate monohydrtate | 35.5 |
| Tetraacetyl ethylenediamine (TAED) | 18.5 |
| Tartaric acid | 18.0 |
| Teric 305 (Huntsman Chemicals Inc) Alkylphenol polyethoxylate phosphate | 3.0 |
| Flurad flurosurfactant (DuPont Inc.) | 0.1 |
| Lithium carbonate | 15.6 |
| Hyamine 1622 quaternary biocide (Lonza Inc.) | 2.5 |
| Dequest phosphonate chelatant (Monsanto Inc.) | 0.5 |
| Amylase enzyme | 0.05 |
| Urea | 2.0 |
| Sodium sulphate anhydrous | balance |

Circulating Detergent-Disinfectant

| Ingredient | Amount % by weight |
| --- | --- |
| Lithium lactate | 5.0 |
| Trisodium phosphate | 5.0 |
| EDTA Li4 | 0.75 |
| Nitrilotriacetic acid, trisodium salt | 0.75 |
| pyrrolidone | 4.0 |
| Berol 522 (nonionic - cationic blend) AZKO Nobel Inc. | 3.5 |
| Dimethyldodecylamine glycolate | 2.0 |
| Dodecyl alcohol (defoaming agent) | 0.15 |
| Ethyleneglycol ethylether | 3.5 |
| Lithium methyl methacrylate | 1.0 |
| Water | balance |

Acidic Detergent-Disinfectant

| Ingredient | Amount % by weight |
| --- | --- |
| Lithium glycolate | 20.0 |
| EDTA acid | 1.0 |
| alkyl C12 amine oxide | 5.5 |
| Flurad SBN | 0.1 |
| Lauryldimethylamine hydrochloride | 2.5 |
| Hexylene glycol | 7.5 |
| Triethanolamine hydrochloride | 3.0 |
| Dodecyl alcohol (defoaming) | 0.15 |
| Water | balance |

The above compositions were evaluated using the same method as set out in Example 1. The results indicated that these compositions were effective against biofilms.

It will be obvious to those well versed in the art that modifications of the formulations of the compositions described herein can be made without departing from the scope and principles disclosed in this specification. All such variations are considered within the scope of the invention described in this patent disclosure.

What is claimed is:

1. A medical residue treatment composition which includes:

at least one surfactant present in a range of about 0.05% to 15% by weight;

at least one solvent;

at least one co-solvent;

at least one nitrogen containing biocide present in an amount from 0.5% to 20% by weight; and at least one organic chelating agent selected from the lithium salts of hydroxyorganic or organic acids; the lithium salts of a carbonate or bicarbonate or mixtures thereof; the lithium salts of carboxylated and substituted diethylamine; the lithium salts of substituted derivatives of ethylenediamine, lithium lactate, and dilithium citrate; lithium lauryl sulphate; lithium hydroxide; lithium triphosphate; lithium citrate; lithium tartrate; lithium methylmethacrylate; lithium glycolate; lithium acetate; lithium phosphate; and trilithium trinitriloacetate.

2. A composition according to claim 1 wherein said at least one organic chelating agent is present in an amount from about 0.05% to 5.0% by weight.

3. A composition according to claim 1 wherein said at least one nitrogen containing biocide is selected from an alkyl (C8–14)dimethyl benzylammonium halide; a dialky (C4–10)di- or trimethylbenzyl or ethylbenzyl ammonium halide; an alkyl (C10–18)amine halide or other recognized commercial quaternary ammonium halide, including chlorhexidine salts and benzethonium chloride (Hyamine 1622).

4. A composition according to claim 1 wherein said at least one nitrogen containing biocide is selected from an alkyl (C8–18)dimethylbenzyl ammonium chloride; cetyl trimethyl ammonium bromide; cetyl pyrimidium bromide; cetyl pyrimidium iodide; a dimethyl dialkyl (C6–18) ammonium chloride; chlorhexidine diacetate; chlorhexidine digluconate; dodecylamine hydrochloride; dodecylamine gluconate; dimethyldodecylamine hydrochloride or glycolate; methyl bisthiocyanate; betabromo or betanitrostyrene; tetrachloro isonaphalonitrile; 2-bromo-2-nitro-1,3-propanol; 5-chloro-4-isothiazolin-3one; and 2-methyl-4-isothiazolin-3one.

5. A composition according to claim 1 wherein said at least one surfactant is selected from an alkyl polysaccharide surfactant; a nonionic surfactant; an alkyl, aryl or amine halide surfactant; a polyethoxylate of an alkylamine surfactant, and a lauric mono, di- or triethanolamine.

6. A composition according to claim 1 wherein said at least one surfactant selected from a nonionic surfactant containing from 8 to 18 carbon atoms and/or from 6 to 12 moles of ethyleneoxide; an amine oxide containing from 12 to 18 carbon atoms; an ethoxyalte alkyl amine containing from 10 to 14 carbon atoms and 1 to 6 moles of ethylene oxide; an alkyl (C8–12) dimethyl benzyl amine halide; and a lauric mono, di- or triethanolamine.

7. A composition according to claim 1 wherein said at least one solvent is selected from one or more low molecular weight polar water soluble solvents chosen from primary or secondary alcohols; glycols; esters; ketones; aromatic alcohols; and cyclic nitrogen solvents containing 8 or less carbon atoms.

8. A composition according to claim 1 wherein said at least one solvent is selected from a (C1–6) alcohol; ester; ether; ketone; glycol; or their methyl and ethyl esters and ethers; an aromatic alcohol containing 8 or less carbon atoms; pyrrolidone; and methyl pyrrolidone.

9. A composition according to claim 1 wherein said at least one solvent is present in an amount from about 1.0% to 20% by weight.

10. A composition according to claim 1 wherein said at least one co-solvent is selected from one or more amines or amine derivatives of an acetamide; acetyl acetamide or diethylacetamine; pyrrolidone or methyl pyrrolidine; urea; a mono, di- or triethanolamine; and isopropanolamine or their halides.

11. A composition according to claim 1 which includes at least one co-solvent present in an amount from about 1.0% to 20% by weight.

12. A medical residue treatment composition which includes:
- at least one surfactant present in an amount from 0.01% to 20% by weight;
- at least one solvent;
- at least one co-solvent;
- at least one nitrogen containing biocide present in an amount from 0.025% to 20% by weight; and
- at least one organic chelating agent selected from lithium bicarbonate, from about 0.05%–10.0% by weight; lithium carbonate, from about 0.05%–25.0% by weight; lithium phosphate, from about 0.10%–110.0% by weight; lithium glycolate, from about 0.05%–5.0% by weight; lithium lactate, from about 0.05%–5.0% by weight; lithium citrate, from about 0.05%–7.5% by weight; lithium tartrate, from about 0.05%–5.0% by weight; lithium methylmethacrylate, from about 0.05%–5.0% by weight; lithium benzoate, from about 0.05%–2.5% by weight; lithium lauryl sulphate, from about 0.05%–4.0% by weight; lithium alkylarylsulphonate, from about 0.05%–10.0% by weight; and Lithium Dowanol 3B0 dialkyl (C2–8) diphenoloxide disulfonate, from about 0.05%–10.0% by weight.

* * * * *

UNITED STATES PATENT AND TRADEMARK OFFICE
CERTIFICATE OF CORRECTION

PATENT NO. : 6,855,678 B2  Page 1 of 1
APPLICATION NO. : 10/347858
DATED : February 15, 2005
INVENTOR(S) : Reginald Keith Whiteley It is certified that error appears in the above-identified patent and that said Letters Patent is hereby corrected as shown below:

Title Page, Item (76) Inventor name should read:

-- Reginald Keith Whiteley --

Signed and Sealed this

Eighth Day of June, 2010

David J. Kappos
*Director of the United States Patent and Trademark Office*